United States Patent [19]

Kleinpeter

[11] 4,123,448

[45] Oct. 31, 1978

[54] ADIABATIC REACTOR

[75] Inventor: Joseph A. Kleinpeter, McMurray, Pa.

[73] Assignee: Continental Oil Company, Stamford, Conn.

[21] Appl. No.: 802,383

[22] Filed: Jun. 1, 1977

[51] Int. Cl.² ............................................. C07C 1/04
[52] U.S. Cl. ........................... 260/449 M; 260/449 S; 260/449.6 M; 422/212
[58] Field of Search .................. 260/449 M, 449.6 M, 260/449 S

[56] References Cited

U.S. PATENT DOCUMENTS

| | | | |
|---|---|---|---|
| 1,923,865 | 8/1933 | Handforth | 108/DIG. 1 |
| 2,330,767 | 9/1943 | Weltz | 23/288 R X |
| 2,602,811 | 7/1952 | Montgomery et al. | 260/449 S |
| 3,274,275 | 9/1966 | Hutto et al. | 208/DIG. 1 |
| 3,511,624 | 5/1970 | Humphries et al. | 260/449 M |
| 3,725,653 | 4/1973 | Carr et al. | 208/DIG. 1 |
| 3,870,738 | 3/1975 | Yamamoto et al. | 260/449 S |
| 3,890,113 | 6/1975 | Child et al. | 260/449 M |
| 3,967,936 | 7/1976 | Tajbl | 260/449 M |

FOREIGN PATENT DOCUMENTS 518,050  11/1955  Canada ................................. 260/449.6

*Primary Examiner*—Howard T. Mars
*Attorney, Agent, or Firm*—F. Lindsey Scott; William A. Mikesell, Jr.; D. Leigh Fowler, Jr.

[57] ABSTRACT

An improved adiabatic reactor for exothermic catalytic reactions is disclosed. The improvement in the reactor comprises the use of multiple injection devices to inject additional reactant streams into the reactor at a plurality of locations at which the reaction is substantially complete. A method for using the reactor is also disclosed.

8 Claims, 4 Drawing Figures

ADIABATIC REACTOR

This invention relates to an improved reactor.

This invention further relates to an improved adiabatic reactor for exothermic catalytic reactions wherein the reactor includes means for injecting a plurality of reactant streams into the reactor at a plurality of locations to thereby improve the efficiency of the reactor.

This invention also relates to a method for improving the effectiveness of an adiabatic reactor used for exothermic catalytic reactions.

In a variety of industrial applications, adiabatic reactors are used for exothermic catalytic reactions. In the reaction of carbon oxide and hydrogen to form methane, for instance, adiabatic reactors are used to catalytically react the carbon oxides and hydrogen to produce methane. Such reactions liberate large amounts of heat and as a result, the feed stream to the reactor is normally adjusted to a composition such that complete reaction of the reactants in the stream results in a temperature in the catalyst bed which is below the maximum temperature tolerable by the catalyst. It has been observed, however, that in such reactors only a minor portion of the catalyst bed is used initially and that the reaction products, including any water produced and the like, pass through the remainder of the catalyst bed thereby subjecting the bulk of the catalyst bed to detrimental effects resulting from the passage of substantial amounts of heated vapors, including water, over the catalyst with no increased efficiency in the reaction. Earlier attempts to modify the temperature in the reactor have involved the addition of streams of diluent or, optionally, streams of additional reactant materials at fixed locations within the catalyst bed.

It has now been found that an improved catalyst efficiency is achieved in the use of a reactor which includes a catalyst zone; injection means positioned along the length of the catalyst zone; and a plurality of temperature sensors positioned along the catalyst zone by an improvement comprising; operatively associating a temperature monitoring means with the temperature sensors so that the temperature in a catalyst bed positioned in the catalyst zone is monitored to detect locations within the catalyst bed at which the catalyst bed temperature has reached a substantially constant value with the temperature monitoring means being operatively associated with an injection controller means so that additional fluid reactant streams are injected into the reactor in the constant temperature zones.

In the use of such reactors, the reactants are injected into a first end of the reactor and the temperature in the reactor is monitored to determine the length of catalyst bed required for the reactant stream to reach substantial equilibrium. Additional reactant streams are then injected beyond the point at which equilibrium is reached and the temperature monitored until the combined streams reach substantial equilibrium. A plurality of such equilibrium points and injections can be used to utilize substantially the entire length of the catalyst bed for reaction.

In the description of the FIGS., the same numbers will be used throughout to refer to the same or similar components.

Figure 1:
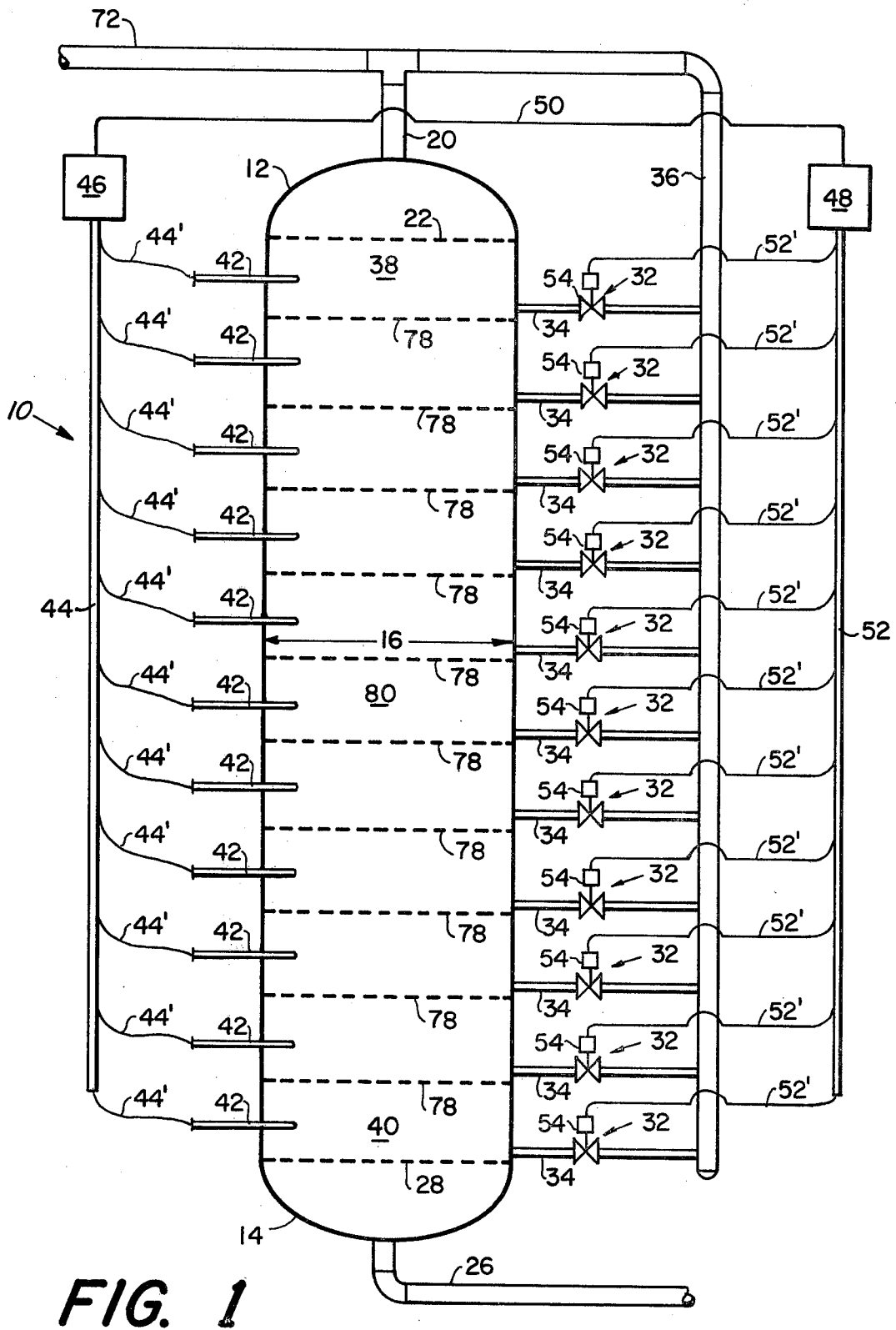
FIG. 1 is a schematic view of an embodiment of the improved reactor of the present invention.

FIG. 1 is a schematic view of the improved reactor 10 of the present invention. Reactor 10 includes a first end 12 and a second end 14 with a catalyst zone 16 being positioned between first end 12 and second end 14. Reactor 10, as shown, includes an inlet pipe 20, an inlet flow distribution plate 22, a catalyst support 28 and an outlet pipe 26 and is equipped with a plurality of injection devices 32 positioned between first end 12 and second end 14 of reactor 10. Injection devices 32 comprise injection pipes 34 in fluid communication with a reactant supply pipe 36 and catalyst zone 16 with flow through pipes 34 being controlled by injection control valves 54. Injection devices 32 are positioned to achieve the injection of reactant streams between a first end 38 of catalyst zone 16 and a second end 40 of catalyst zone 16. Reactor 10 is also equipped with a plurality of temperature sensors 42 which are positioned to sense the temperature in catalyst zone 16 and are connected by a plurality of connectors 44' to a connector bundle 44 which is in electrical contact with a temperature monitoring means 46. Temperature monitoring means 46 is operatively joined to an injection controller means 48 by a connector 50. Injection controller means 48 is operatively joined to a plurality of injection control valves 54 by a connector bundle 52 and a plurality of connectors 52'.

Figure 2:
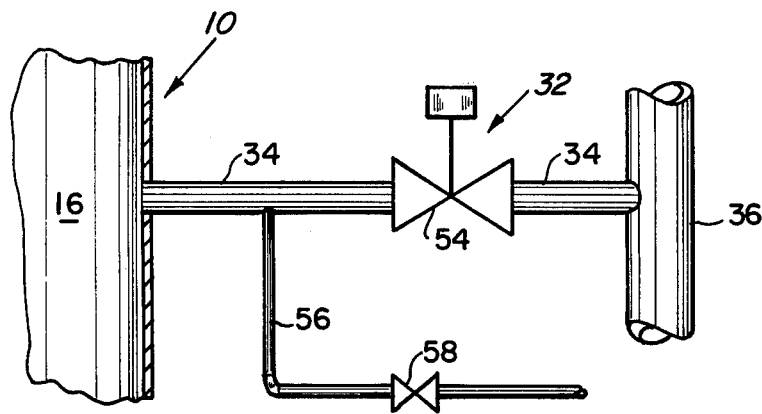
FIG. 2 is a schematic view of a reactant stream injection arrangement.

Referring now to FIG. 2, an injection device 32 is shown. Device 32 comprises an injection pipe 34 fluidly communicating reactor 10 and a reactant supply pipe 36 with an injection control valve 54 being positioned in pipe 34. A water injection pipe 56 containing a water injection control valve 58 is shown fluidly communicating a water supply (not shown) and pipe 34 so that the water composition in the reactant streams injected can be varied. It is to be clearly understood that other reactants or inert diluents such as methane and the like could be injected into a reactant stream in line 34 via line 56 although the discussion herein has been directed to the variation of the water composition in the reactant stream in pipe 34.

Figure 3:
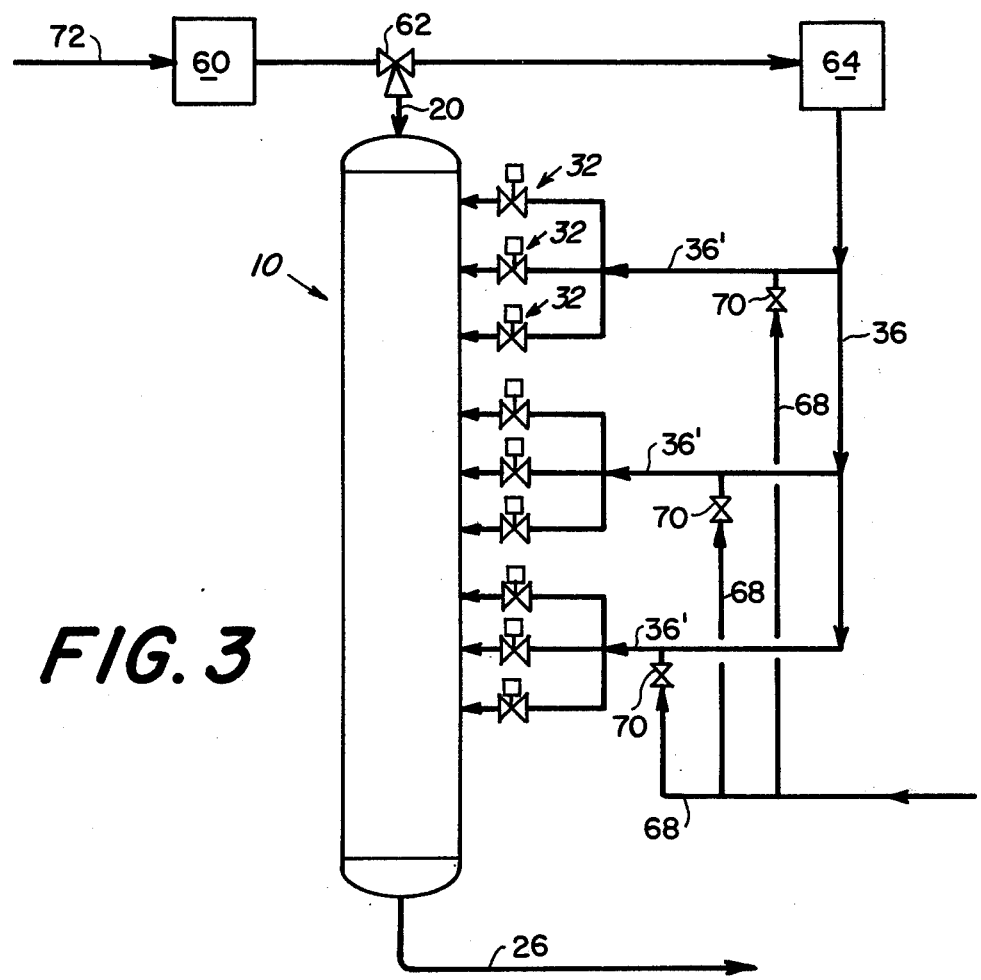
FIG. 3 is a schematic view of an embodiment of the reactor of the present invention wherein the reactant stream composition is adjusted.

With respect to FIG. 3, a schematic view of an alternative embodiment of reactor 10 is shown. A condenser 60 is provided in a reactant feed line 72 to vary the water content of a reactant feed stream. A valve 62 is provided to control the amount of feed stream charged to reactor 10 and to a second condenser 64. Second condenser 64 is in fluid communcation with a reactant supply pipe 36 which is connected to three groups of injection devices 32 for the injection of reactant feed streams into three zones of reactor 10. Clearly, a multiplicity of such zones could be provided or the injection devices could be individually linked to reactant supply pipe 36 as in FIG. 1. The use of condensors 60 and 64 permits a variation in the water content of a reactant stream charged to reactor 10 via injection devices 32. Means are provided for further varying the composition of the reactant streams charged in the form of lines 68 which are joined to lines 36' which are in fluid communication with line 36. Control valves 70 are provided for regulating the flow of diluents, other reactants or the like passed through lines 68. Clearly the composition of the reactant streams can be varied in many ways within the scope of the present invention.

With reference to FIG. 1, reactant feed distribution means 78 are shown in conjunction with injection devices 32 so that the injected reactants are distributed relatively uniformly across the cross-sectional area of a catalyst bed 80 at the point of injection. Such is obviously desirable to prevent localized zones of high reaction rate, high temperature and the like. Such zones of high temperature and the like are detrimental to many catalysts used in such reactions.

Catalyst bed 80 is typically positioned in reaction zone 16 and is selected from those catalysts effective with the reaction contemplated by the users of the reactor.

In the use of reactor 10, a reactant feed stream is passed to reactor 10 through reactant feed line 72, inlet pipe 20 and flow distributor 22. As reaction occurs in catalyst bed 80, the temperature in catalyst bed 80 will rise to a substantially constant value determined by the composition, temperature and pressure of the injected reactant feed stream. As soon as the reaction has reached substantial completion, the temperature will assume a substantially constant value throughout the remainer of reactor 10. Temperature sensors 42 are monitored by temperature monitoring means 46 to detect such zones of substantially constant temperature and when such zones are detected, additional reactant materials are introduced through an injection device positioned in such zones of substantially constant temperature. Desirably, the additional reactants are injected at some predetermined distance beyond the point at which the reaction has reached substantial equilibrium as indicated by the attainment of a substantially constant temperature. The injection of the reactant materials will usually result in a substantial temperature drop at the point of injection (the reactants are usually below the catalyst bed temperature), with the temperature rising to a substantially constant value again as the additional reactants react to attain substantial equilibrium. The temperature will, at this point, have reached a substantially constant value again and the process is repeated with a plurality of injections through injection devices 32 being used to result in the use of substantially the entire length of catalyst bed 80 for reaction. The monitoring of the temperature profile, control of the injection points, and the like may be performed manually, but is desirably performed by automated process control equipment known to the art such as computers and the like.

Figure 4:
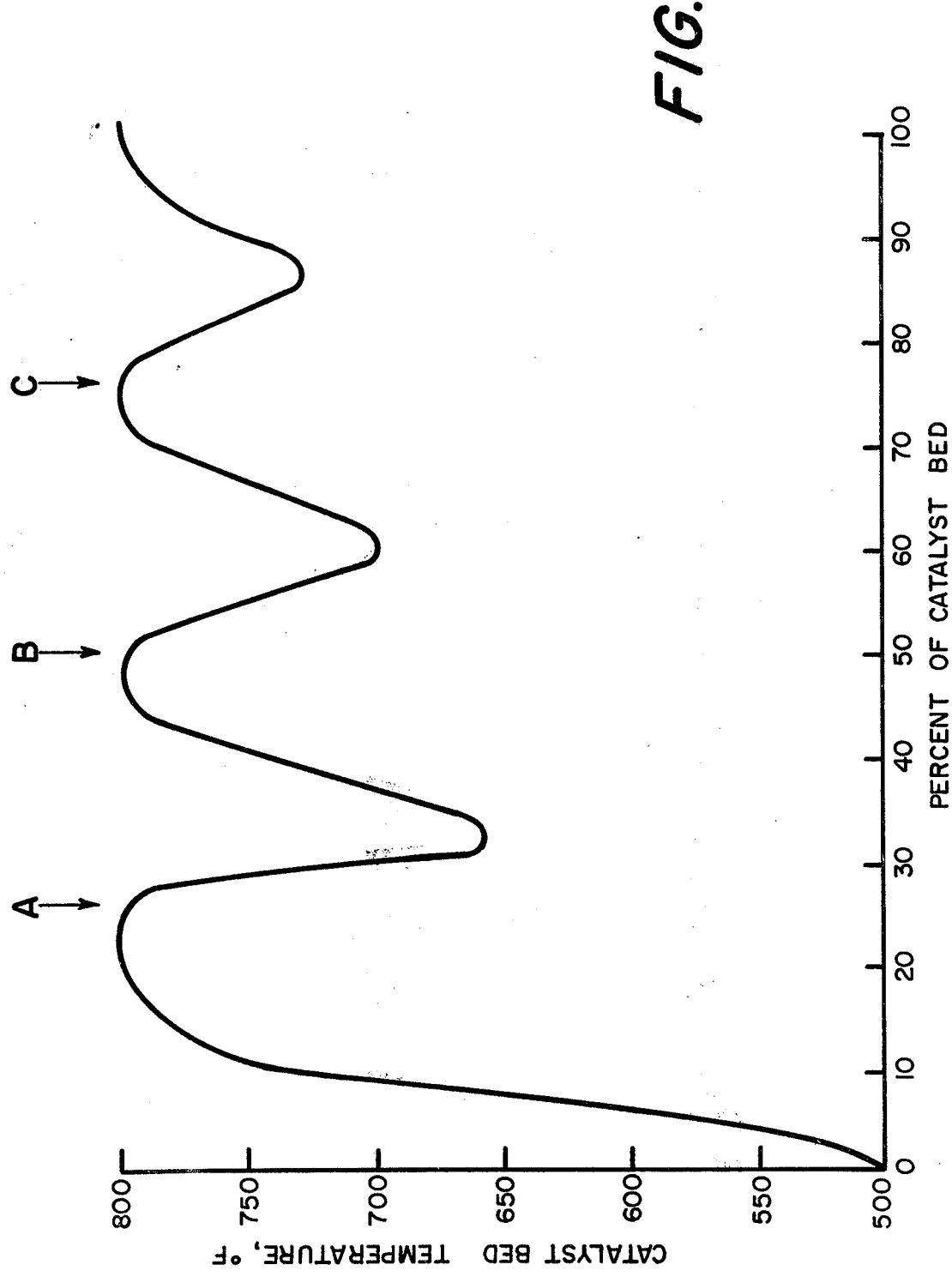
FIG. 4 is a chart showing the temperature profile in a catalyst bed as utilized in the improved reactor of the present invention.

With reference to FIG. 4, a typical temperature profile utilizing the method of the present invention is shown. It will be noted that the temperature rises rapidly to a substantially constant value as the reaction occurs and thereafter at points A, B and C, additional reactants are injected causing the temperature to drop precipitately and thereafter rise to a substantially constant value when the reaction is substantially completed again.

It is highly desirable that the stream of reaction products leave the catalyst bed at a substantially constant temperature. In other words, the injection of additional reactant material should be controlled so that a sufficient length of catalyst bed remains beyond the last reactant injection point so that substantially complete reaction is achieved.

In the practice of the present invention, it is recognized that in many instances it may be desirable to vary the composition of the reactant streams added along the length of catalyst bed 80 from the composition of the reactant stream injected initially. Means for so adjusting the composition are shown in FIG. 2 and comprise a piping arrangement whereby additional reactant materials can be injected via an injection device 32. FIG. 3 shows a further arrangement for adjusting the composition of the reactant feed streams and also shows a variation in piping arrangements which may be considered desirable in some instances whereby injection devices 32 are joined to separate piping systems for providing a controlled feed to a plurality of injection devices. Each bank of injection devices is directed to a particular zone and the flexibility achieved in such an arrangement is somewhat less than in the arrangement shown in FIG. 1. However, in some instances, it may be desirable to use such variations to achieve greater flexibility in varying the composition of the reactant stream injected along the length of catalyst bed 80.

In a particularly desirable embodiment of the present invention, the reaction conducted is a methanation reaction wherein oxides of carbon are reacted with hydrogen over a catalyst in a reaction zone to produce methane.

The catalysts typically are selected from those catalysts comprising nickel, cobalt and mixtures thereof supported on alumina, silica, kiesulguhr or mixtures of such catalyst supports. A variety of such catalysts are known to those skilled in the art and need not be discussed further except to note that such catalysts are useful in the reactor and method of the present invention. Some such catalysts are shown in U.S. Pat. No. 3,890,113, issued June 17, 1975 to Child et al. and U.S. Pat. No. 3,922,148 issued Nov. 25, 1975 to Child, which are hereby incorporated by reference.

In the reaction of carbon oxides with hydrogen to form methane, considerable quantities of heat are liberated during the reaction and accordingly the reactor of the present invention is ideally suited to such reactions. Further, it is desirable in such reactions that the composition of the reactant streams be controlled so that the temperatures in the reactor are kept below those temperatures at which the catalyst is damaged. Further, it is necessary that the composition of the reactant stream be kept within limits known to those skilled in the art so that carbon deposition on the catalyst, high temperatures and the like are avoided. The reactant stream typically comprises $CO$, $CO_2$, $H_2$, $H_2O$, $CH_4$, $C_2H_4$, $C_2H_6$, $N_2$ and the like. Typically, the reactant stream is controlled to a carbon oxide-hydrogen composition such that carbon deposition is minimized and catalyst bed temperatures are below the maximum permissible. In such processes heretofore, no effort has been made to determine the point at which the reaction is complete so that additional reactant materials can be injected at such point. Such results in the bulk of the catalyst bed on a fresh catalyst charge being subjected to the flow of reaction products containing water and the like, at a high temperature for prolonged periods of time before the catalyst is used. As is known to those skilled in the art, exposure of the catalyst to the equilibrium water produced in such reactions at elevated temperature is damaging to the catalyst. In other words, the reaction is substantially complete within the first portion of the catalyst bed with the remainder of the catalyst bed being unused until the first portion of the catalyst bed has been contaminated or otherwise rendered inactive. Clearly, by the method of the present invention, this disadvantage is overcome and further it is possible as shown in FIGS. 2 and 3 to vary the composition of the reactant streams to have greater or lesser amounts of water, to contain greater or lesser amounts of reactant material per unit volume than the initially injected reaction stream or the like. In summary, the present invention provides an improved reactor and a method for using the improved reactor whereby greatly improved catalyst efficiency is achieved and wherein a flexibility of operation unknown heretofore is provided.

It is pointed out that the embodiments described hereinbefore are illustrative rather than limiting in nature and that many variations and modifications are possible within the scope of the present invention. It is anticipated that many such variations and modifications may appear obvious and desirable to those skilled in the art upon a review of the foregoing description of preferred embodiments and the following examples.

EXAMPLES

A series of computer test runs simulating the use of the reactor and method of the present invention were conducted to demonstrate the operation of the reactor and method of the present invention.

EXAMPLE 1

100 Mols of a gaseous reactant stream at the temperature and having the composition shown below in Table I as ($A_1$ in) is injected into a catalyst zone in a reactor and reacted to produce an equilibrium mixture having a composition and temperature shown as ($A_1$ eq). Downstream from the point at which equilibrium is achieved, 100 mols of a second gaseous reactant stream having the same composition and temperature as ($A_1$ in) is injected and mixes with stream ($A_1$ eq) to produce a reactant mixture having the temperature and composition shown as ($A_2$ in) which reacts to produce an equilibrium mixture ($A_2$ eq) having the temperature and composition shown below. Similarly, 100 mols of a third gaseous stream having the same temperature and composition as ($A_1$ in) is injected and mixes with stream ($A_2$ eq) to produce a reactant mixture ($A_3$ in) which reacts to produce an equilibrium mixture ($A_3$ eq). 100 Mols of a fourth gaseous stream having the same temperature and composition as ($A_1$ in) is injected and mixes with equilibrium mixture ($A_3$ eq) to produce a reactant mixture ($A_4$ in) which reacts to produce an equilibrium mixture ($A_4$ eq) which is the reactor product.

TABLE I

| Stream | $H_2$ Mol % | $CH_4$ Mol % | CO Mol % | $CO_2$ Mol % | $H_2O$ Mol % | $N_2$ Mol % | $C_2+$ Mol % | Temp. °F. |
|---|---|---|---|---|---|---|---|---|
| $A_1$ in | 15.85 | 74.08 | 2.84 | 1.74 | 2.79 | 2.47 | 0.23 | 500 |
| $A_1$ eq | 4.08 | 84.37 | 0.05 | 0.94 | 7.89 | 2.67 | 0.00 | 800 |
| $A_2$ in | 10.19 | 79.03 | 1.50 | 1.36 | 5.24 | 2.56 | 0.12 | 653 |
| $A_2$ eq | 4.12 | 84.34 | 0.06 | 0.95 | 7.87 | 2.66 | 0.00 | 800 |
| $A_3$ in | 8.23 | 80.75 | 1.03 | 1.23 | 6.09 | 2.60 | 0.08 | 702 |
| $A_3$ eq | 4.16 | 84.31 | 0.06 | 0.96 | 7.85 | 2.66 | 0.00 | 799 |
| $A_4$ in | 7.25 | 81.61 | 0.79 | 1.17 | 6.51 | 2.61 | 0.06 | 726 |
| $A_4$ eq | 4.20 | 84.28 | 0.06 | 0.97 | 7.83 | 2.66 | 0.00 | 798 |

By the use of the method of the present invention, four equal streams have been reacted in a reactor utilizing substantially the whole length of the catalyst bed instead of only the portion of the catalyst bed first contacted by the reactants. The reactor efficiency is also improved since the temperature rise is not localized, thus greater quantities of carbon monoxide can be converted in the reactor than in reactors which receive only a single stream charge.

EXAMPLE 2

A series of runs similar to those of Example 1 were conducted except that the gaseous streams added to produce the streams corresponding to ($A_2$ in), ($A_3$ in) and ($A_4$ in) were substantially dry. 100 Mols of a gaseous stream having the composition and temperature shown below in Table II as ($B_1$ in) is injected into a catalyst zone in a reactor and reacted to produce an equilibrium mixture ($B_1$ eq). Downstream from the point at which equilibrium is achieved, 100 mols of a dry second gaseous reactant stream which has the same composition as ($B_1$ in) on a dry basis is injected and mixes with ($B_1$ eq) to produce a reactant mixture ($B_2$ in) having the composition and temperature shown below which reacts to produce an equilibrium mixture ($B_2$ eq). 100 Mols of a dry third reactant stream having the same composition as ($B_1$ in) on a dry basis is injected to produce a reactant mixture ($B_3$ in) which reacts to produce an equilibrium mixture ($B_3$ eq). 100 Mols of a third dry gaseous reactant stream having the same composition as ($B_1$ in) on a dry basis is injected to produce a reaction mixture ($B_4$ in) which reacts to produce an equilibrium mixture ($B_4$ eq) which is the reactor product.

TABLE II

| Stream | $H_2$ Mol % | $CH_4$ Mol % | CO Mol % | $CO_2$ Mol % | $H_2O$ Mol % | $N_2$ mol % | $C_2+$ Mol % | Temp. °F. |
|---|---|---|---|---|---|---|---|---|
| $B_1$ in | 15.85 | 74.08 | 2.84 | 1.74 | 2.79 | 2.47 | 0.23 | 500 |
| $B_1$ eq | 4.08 | 84.37 | 0.05 | 0.94 | 7.89 | 2.67 | 0.00 | 800 |
| $B_2$ in | 10.42 | 80.13 | 1.54 | 1.38 | 3.80 | 2.60 | 0.13 | 653 |
| $B_2$ eq | 3.97 | 85.79 | 0.06 | 0.91 | 6.56 | 2.71 | 0.00 | 806 |
| $B_3$ in | 8.30 | 82.43 | 1.07 | 1.22 | 4.26 | 2.65 | 0.08 | 706 |
| $B_3$ eq | 3.95 | 86.26 | 0.07 | 0.90 | 6.11 | 2.72 | 0.00 | 807 |
| $B_4$ in | 7.22 | 83.59 | 0.82 | 1.14 | 4.79 | 2.67 | 0.06 | 733 |
| $B_4$ eq | 3.96 | 86.47 | 0.07 | 0.90 | 5.87 | 2.73 | 0.00 | 808 |

By comparison of the water content of the gaseous streams passing through the reactor in Example 1 with those in Example 2, it is clear that, while substantially the same amount of CO has been reacted, the water content of the gaseous streams in contact with the catalyst is much lower. Since water is detrimental to catalyst life, the use of the technique demonstrated above should be beneficial in most instances in extending catalyst life.

EXAMPLE 3

100 Mols of a gaseous reactant stream having the temperature and composition shown below in Table III as ($C_1$ in) is injected into a catalyst bed in a reactor and reacted to produce an equilibrium mixture having a composition and temperature shown as ($C_1$ eq) below. 25 Mols of a dry gaseous reactant stream having the composition and temperature shown as ($C_2$) below is injected and mixes with $C_1$ eq to produce a reactant stream ($C_2$ in) having the composition and temperature shown which reacts to produce an equilibrium mixture ($C_2$ eq). An additional 25 mols of ($C_2$) is injected and mixes with ($C_2$ eq) to produce a reactant mixture ($C_3$ in) which reacts to produce an equilibrium mixture ($C_3$ eq). A further 25 mols of $C_2$ is injected and mixes with ($C_3$ eq) to produce a reactant mixture ($C_4$ in) which reacts to produce an equilibrium mixture ($C_4$ eq) which is the reactor product.

TABLE III

| Stream | $H_2$ Mol % | $CH_4$ Mol % | CO Mol % | $CO_2$ Mol % | $H_2O$ Mol % | $N_2$ Mol % | $C_2+$ Mol % | Temp. °F. |
|---|---|---|---|---|---|---|---|---|
| $C_1$ in | 15.85 | 74.08 | 2.84 | 1.74 | 2.79 | 2.47 | 2.47 | 500 |
| $C_1$ eq | 4.08 | 84.37 | 0.05 | 0.94 | 7.89 | 2.67 | 0.00 | 800 |
| $C_2$ | 66.02 | 11.93 | 14.72 | 5.00 | 0.00 | 1.09 | 1.24 | 300 |
| $C_2$ in | 17.24 | 66.98 | 3.17 | 1.80 | 6.22 | 2.33 | 0.26 | 728 |
| $C_2$ eq | 9.06 | 76.60 | 0.41 | 1.89 | 9.57 | 2.47 | 0.00 | 959 |
| $C_3$ in | 19.53 | 64.72 | 3.04 | 2.46 | 7.81 | 2.21 | 0.23 | 878 |
| $C_3$ eq | 13.47 | 70.26 | 1.03 | 2.51 | 10.47 | 2.31 | 0.00 | 1050 |
| $C_4$ in | 21.93 | 60.87 | 3.23 | 2.91 | 8.75 | 2.11 | 0.20 | 969 |
| $C_4$ eq | 17.06 | 65.19 | 1.72 | 2.87 | 10.97 | 2.19 | 0.00 | 1107 |

The use of reactant streams containing higher concentrations of $H_2$ and CO as shown above results in improved reactor efficiency in those instances where the catalyst used can tolerate temperatures in excess of 1000° F.

EXAMPLE 4

A further series of tests were run similar to those in Example 3 with the exception that 10 mols of methane was substituted for stream $C_2$ in each instance and the first inlet stream is richer in CO and $H_2$ than ($C_1$ in). Test results are set forth in Table IV.

TABLE IV

| Stream | $H_2$ Mol % | $CH_4$ Mol % | CO Mol % | $CO_2$ Mol % | $H_2O$ Mol % | $N_2$ Mol % | $C_2+$ Mol % | Temp. °F. |
|---|---|---|---|---|---|---|---|---|
| $E_1$ in | 43.38 | 39.73 | 8.53 | 4.24 | 1.88 | 1.68 | 0.56 | 500 |
| $E_1$ eq | 22.86 | 56.37 | 3.09 | 3.32 | 12.39 | 1.97 | 0.00 | 1198 |
| $E_2$ | | 100.00 | | | | | | 300 |
| $E_2$ in | 20.46 | 60.95 | 2.77 | 2.97 | 11.09 | 1.76 | 0.00 | 1100 |
| $E_2$ eq | 19.10 | 62.18 | 2.17 | 3.08 | 11.70 | 1.78 | 0.00 | 1143 |
| $E_3$ in | 17.27 | 65.80 | 1.96 | 2.78 | 10.58 | 1.61 | 0.00 | 1061 |
| $E_3$ eq | 16.13 | 66.81 | 1.52 | 2.83 | 11.09 | 1.62 | 0.00 | 1094 |
| $E_4$ in | 14.71 | 69.74 | 1.39 | 2.58 | 10.11 | 1.48 | 0.00 | 1025 |
| $E_4$ eq | 13.75 | 70.57 | 1.07 | 2.57 | 10.55 | 1.49 | 0.00 | 1050 |

Pure methane, optimally recycled product SNG, is used to moderate the reactor temperature when reactant streams rich in CO and $H_2$ are used. The use of the methane injections serves to lower the reactor temperature which is beneficial to higher methane yields at equilibrium.

Having thus described the invention, I claim:

1. A method for improving the efficiency of an adiabatic, catalytic reactor for exothermic reactions, wherein said reactor includes a catalyst bed, positioned in said reactor, said method comprising;
    (a) passing a first fluid reactant stream comprising carbon oxides, hydrogen, and water into a first end of said catalyst bed at reaction conditions so that said carbon oxides and hydrogen react to form methane as the stream passes along the length of said catalyst bed toward a second end of said catalyst bed;
    (b) determining a first location in said catalyst bed at which the catalyst temperature has increased to a substantially constant value;
    (c) injecting a second fluid reactant stream comprising carbon oxides, hydrogen and water into said catalyst bed between said first location and said second end of said catalyst bed;
    (d) determining a second location in said catalyst bed at which the catalyst temperature has increased to a substantially constant value, said second location being between the point at which said second fluid reactant stream is introduced and said second end of said catalyst bed;
    (e) injecting a third fluid reactant stream comprising carbon oxides, hydrogen and water between said second location and said second end of said catalyst bed; and,
    (f) recovering methane from said reactor.

2. The method of claim 1 wherein additional locations at which the temperature in said catalyst bed has reached a substantially constant value are determined and wherein at least one additional fluid reactant stream is injected between at least two of said locations.

3. The method of claim 2 wherein the temperature of said catalyst bed has reached a substantially constant value at said second end of said catalyst bed.

4. The method of claim 1 wherein said second fluid reactant stream comprises CO, $CO_2$, $CH_4$, $H_2O$, $N_2$, $C_2H_4$, $C_2H_6$, and $H_2$.

5. The method of claim 2 wherein said third fluid reactant stream comprises CO, $CO_2$, $H_2$, $H_2O$, $CH_4$, $C_2H_4$, $C_2H_6$, and $N_2$.

6. A method for improving the efficiency of an adiabatic catalytic reactor for reacting carbon oxides with hydrogen to produce methane, said method comprising:
    (a) passing a first fluid reactant stream comprising carbon oxides, hydrogen, and water into catalyst bed positioned in said reactor;
    (b) determining the length of catalyst bed required for said first fluid reactant stream to reach substantial equilibrium;
    (c) injecting a second fluid reactant stream comprising carbon oxides, hydrogen and water downstream of the point at which substantial equilibrium has been accomplished;
    (d) determining the length of catalyst bed required for said second fluid reactant stream to reach substantial equilibrium;
    (e) injecting a third fluid reactant stream comprising carbon oxides, hydrogen and water downstream of the point at which said second fluid reactant stream has reached substantial equilibrium; and
    (f) recovering methane from said reactor.

7. The method of claim 6 wherein a plurality of additional fluid reactant streams comprising carbon oxides, hydrogen and water are injected along the length of said catalyst bed at points at which substantially complete reaction has been accomplished.

8. The method of claim 7 wherein said fluid reactant streams comprise CO, $CO_2$, $H_2O$, $CH_4$, $N_2$, $C_2H_4$, $C_2H_6$ and $H_2$.

* * * * *